United States Patent [19]

Hall et al.

[11] Patent Number: 5,726,308
[45] Date of Patent: Mar. 10, 1998

[54] HIGH PURITY FORMULATIONS OF HIGHLY SUBSTITUTED LITHIUM AMIDE BASES

[75] Inventors: Randy W. Hall, Kings Mountain; Robert S. Wedinger, Gastonia; Terry L. Rathman, Gastonia; James A. Schwindeman, Gastonia, all of N.C.

[73] Assignee: FMC Corporation, Philadelphia, Pa.

[21] Appl. No.: 620,587

[22] Filed: Mar. 22, 1996

Related U.S. Application Data

[60] Provisional application No. 60/002,059, Aug. 9, 1995.
[51] Int. Cl.$^6$ ............................................. C07F 1/02
[52] U.S. Cl. ............... 540/484; 252/182.12; 546/184; 548/400; 556/401; 556/410; 556/412; 564/2; 564/391; 564/392; 564/462; 564/463
[58] Field of Search ............ 252/182.12; 540/484; 546/184; 548/400; 556/401, 410, 412; 564/2, 391, 392, 462, 463

[56] References Cited

U.S. PATENT DOCUMENTS

| | | | |
|---|---|---|---|
| 4,595,779 | 6/1986 | Morrison et al. | 564/2 |
| 5,002,689 | 3/1991 | Metha et al. | 252/182.12 |
| 5,149,457 | 9/1992 | Smith | 252/182.12 |
| 5,420,322 | 5/1995 | Chiu et al. | 556/412 |

*Primary Examiner*—Richard L. Raymond
*Attorney, Agent, or Firm*—Bell Seltzer Intellectual Property Law Group of Alston & Bird LLP

[57] ABSTRACT

A process for preparing high purity solutions of highly substituted lithium amide bases by direct reaction of lithium metal with highly substituted amine bases alone or in an ether solvent, a hydrocarbon solvent or in a mixed ether/hydrocarbon solvent mixture, optionally in the presence of a catalyst selected from tin salts and transition metal salts of Groups 4B, 5B, 6B, 7B, and 8 of the Periodic Table.

15 Claims, No Drawings

HIGH PURITY FORMULATIONS OF HIGHLY SUBSTITUTED LITHIUM AMIDE BASES

CROSS-REFERENCE TO RELATED APPLICATIONS

This application is related to commonly owned provisional application Ser. No. 60/002,059, filed Aug. 9, 1995, now abandoned, and claims the benefit of its earlier filing date under 35 U.S.C. §119(e).

This invention concerns processes for preparing highly substituted lithium amide bases free of organic contaminants or by-products in ethereal, hydrocarbon or ethereal-hydrocarbon solutions, and in an excess of the highly substituted amine base.

Highly substituted lithium amide bases can be expressed by the formula $(R_3M)_xNLi(R^1)_y$, where M=Si or C, R and $R^1$ are alkyl, cycloalkyl and alkylene groups containing 1 to 8 carbon atoms, and x+y=2. $R_3M$ and $R^1$ may be combined (where M=C) to give a divalent alkylene radical, yielding a lithium cyclic alkylene amide where R and $R^1$ taken together may contain 4 to 8 carbon atoms such as the N-lithio salts of pyrrolidine and hexamethyleneimine. Highly substituted or bulky lithium amide bases of this type are used in the preparation of pharmaceutical intermediates and in general organic synthesis.

U.S. Pat. Nos. 4,595,779 and 5,002,689 describe methods for producing highly substituted lithium amide bases in ether or mixed ether/hydrocarbon solvents using lithium metal in dispersed form and an electron carrier compound such as styrene or isoprene. U.S. Pat. No. 5,149,457 describes a method of producing highly substituted lithium amide bases in solely hydrocarbon solvent media by reacting alkyl-lithium compounds, such as n-butyllithium, with highly substituted amine bases, such as diisobutylamine. By-products in the resulting product solutions arising from the process described in the first two patents cited are reduction products of the electron carriers, styrene and isoprene, viz., ethylbenzene and 2-methyl-2-butene. By-products in the product solutions arising from the process in the third patent cited are saturated alkanes resulting from protonation of the alkyllithium compounds by the highly substituted amine bases. The presence of these by-products in the product highly substituted lithium amide base solutions is often detrimental in subsequent applications, primarily because they pose problems in recovery of final pure solvents from recycle streams. Additionally, the alkane by-products, such as butane, are serious environmental and safety concerns.

U.S. Pat. No. 5,420,322 describes a method for circumventing this problem of by-product impurities by directly reacting the highly substituted amine base, i.e., hexamethyldisilazane, with alkali metals above their melting points, in the absence of electron carriers. Thus the reaction temperature for lithium metal is 225° C. and the reactor must be made of steel (molten lithium metal attacks glass) to withstand the pressures required for use with most ordinary solvents, e.g., tetrahydrofuran and cyclohexane. The use of molten lithium metal at these reaction temperatures is hazardous, since inadvertent exposure to the ambient atmosphere would result in instant conflagration. In addition, the process is expensive with respect to energy expended and capital cost of the pressure equipment needed. Also, best results were obtained using an excess of the base, i.e., hexamethyldisilazane, thus necessitating the use of a second solvent to dissolve the reaction product after reaction was cooled to ambient temperature. Also, it should be noted that attempts to catalyze the reaction using iron chloride did not improve the rate of reaction or the yield of product when lithium was the alkali metal.

The present invention provides a process for the preparation of high purity solutions of highly substituted lithium amide bases by direct reaction of lithium metal with highly substituted amine bases in a media selected from excess highly substitiuted amine base, hydrocarbon solvents, ether solvents, and mixed ether/hydrocarbon solvents optionally in the presence of a catalyst selected from tin salts and transition metal salts of Groups 4B, 5B, 6B, 7B, and 8 of the Periodic Table.

This invention unexpectedly provides a process that does not require use of electron carriers or reaction temperatures above the melting point of lithium metal and, in fact, can be carried out at or below the reflux temperature of the desired final solvent, e.g., tetrahydrofuran. In addition, the reaction between lithium metal and hexamethyldisilazane (in stoichiometric or excess highly substituted amine base quantities, no tetrahydrofuran present) can itself be carried out at the reflux temperature of the highly substituted amine base without resorting to the use of reaction temperatures above the melting point of lithium metal. Or, alternatively, THF may be added to the stoichiometric mixture in controlled amounts so as to allow the reflux temperature to be varied between the reflux temperature of THF and the reflux temperature of the stoichiometric mixture. The use of electron carriers is not required. Optionally, the reaction rates may be increased by the use of metal salts, notably tin salts and transition metal salts.

For example, the highly substituted lithium amide base, lithium hexamethyldisilazide (LHS), can be prepared by reacting lithium metal powder, suspended in tetrahydrofuran, with hexamethyldisilazane at 57°–61° C. in the presence of 0.1 mole % (based on the amine) of $FeCl_3$. A near quantitative yield of the desired LHS (30 wt % in THF) is obtained in 3.5–4 hours. By comparison, a 21 hour reaction period is required to obtain a quantitative yield of LHS in the absence of a catalyst under the same reaction conditions. When the reaction temperature is raised by withholding or reducing the amount of the solvent THF the rate of reaction is speeded up considerably. Thus, a "neat" reaction between powdered lithium metal and hexamethyldisilazane results in an 80% yield in only 5 hours at reflux (127°–149° C.). Some THF must be added at this point to promote the reaction to completion due to the insolubility of the product. However, a calculated amount of THF can be included at the start of the reaction to accomplish this goal. Thus, e.g., addition of about two equivalents of THF per mole of lithium or, per mole of HMDS, raises the reaction temperature about 30 degrees and permits the completion of the stoichiometric reaction in about 6–8 hours without the need for a metal catalyst.

An advantage of this invention is it provides a method for producing novel, organic contaminant-free solutions of highly substituted lithium amide bases under economical, mild, reaction conditions by direct reaction of lithium metal with highly substituted amine bases in ethereal solvents of choice such as, e.g., tetrahydrofuran or in mixed ethereal/hydrocarbon solvent media, such as tetrahydrofuran/cyclohexane. The process of this invention is less expensive than prior art processes that employed reaction temperatures above the melting point of the lithium metal and this process does not require the use of an electron carrier or pressure containing reaction equipment.

Transition metal salts of Groups 4B, 5B, 6B, 7B and 8 of the Periodic Table are excellent catalysts for the reaction of lithium metal with highly substituted amine bases. Generally, the lower numbered groups appear to be better catalysts than the higher ones. Thus, the order of reactivity among the transition metals was found to be Ti>Fe>Cu>Co>Zn. The following table depicts the times required to complete the reaction between lithium metal powder and hexamethyldisilazane in THF using these metals as catalysts.

| TM[a] | mole % TM | Time (hrs)[b] |
|---|---|---|
| None | None | 21 |
| Ti | 0.7 | 0.8 |
| Ti | 0.1 | 2.7 |
| Fe | 1.0 | 2.0 |
| Fe | 0.1 | 3.8 |
| Cu | 0.9 | 3.3 |
| Co | 1.0 | 6.2 |
| Zn | 1.0 | 6.5 |

[a]Transition Metal
[b]To completion

A variety of transition metal salts may be employed including those with inorganic anions, such as iron (III) chloride, nickel (II) chloride, iron (II) chloride, cobalt (II) chloride, titanium (IV) chloride, and zinc bromide, as well as those transition metal salts with organic substituents, such as nickel octoate, iron (III) citrate, nickel acetylacetonate, cobalt (II) acetate and titanium tetraisopropoxide, however, the list of transition metal salts useful in the practice of this invention is not limited to the salts here specfically listed.

Other inorganic salts that may be employed not of the transition metal salt category, include, but are not limited to salts such as, aluminum chloride, aluminum bromide, tin (IV) chloride, tin (II) chloride, magnesium chloride, magnesium bromide, lithium chloride, lithium bromide, and lithium iodide.

Generally, the mole % ranges (based on the amine) for these catalysts in the reactions of highly substituted amine bases with lithium metal powder may vary from about 0.01 to about 5 mole %.

Lithium metal may be employed in the form of powder, sand, shot or larger pieces cut from rods or ingots.

Highly substituted amine bases of this invention are secondary amines, including but not limited to, those selected from the group consisting of diisopropylamine, hexamethyleneimine, diisobutylamine, tert-butylmethylamine, tert-butyl-trimethylsilylamine, cyclohexylisopropylamine, cyclohexylmethylamine, allyl-1-phenylethylamine, allyl-(R)-1-phenylethylamine, allyl-(S)-1-phenylethylamine, benzyl-1-phenylethylamine, benzyl-(R)-1-phenylethylamine, benzyl-(R)-1-phenylethylamine, bis-(1-phenylethyl)amine, (+)-bis-[(R)-1-phenylethyl]amine, (−)-bis-[(S)-1-phenylethyl]amine, 2,2,6,6-tetramethylpiperidine, pyrrolidine, piperidine and hexamethyldisilazane.

The process, reacting the above list of amine bases with lithium metal produces highly substituted lithium amide bases which include but are not limited to lithium diisopropylamide, lithium hexamethyleneimide, lithium diisobutylamide, lithium tert-butyl-methylamide, lithium tert-butyl-trimethylsilylamide, lithium cyclohexylisopropylamide, lithium cyclohexylmethylamide, lithium allyl-1-phenylethylamide, lithium allyl-(R)-1-phenylethylamide, lithium allyl-(S)-1-phenylethylamide, lithium benzyl-1-phenylethylamide, lithium benzyl-(R)-1-phenylethylamide, lithium benzyl-(R)-1-phenylethylamide, lithium bis-(1-phenylethyl)amide, lithium (+)-bis-[(R)-1-phenylethyl]amide, lithium (−)-bis-[(S)-1-phenylethyl]amide, lithium 2,2,6,6-tetramethylpiperidide, lithium pyrrolidide, lithium piperidide and lithium hexamethyldisilazide.

Examples of ethereal solvents which may be employed, include but are not limited to, tetrahydrofuran, 2-methyltetrahydrofuran, diethyl ether, t-butylmethyl ether, dibutyl ether, diethoxymethane, 1,2-dimethoxyethane (glyme), diglyme, triglyme, and mixtures thereof.

Examples of liquid hydrocarbon solvents useful in the practice of this invention include, but are not limited to, hexane, cyclohexane, toluene, ethylbenzene, and xylene. Some of the of highly substituted lithium amide bases, such as lithium diisobutylamide and lithium hexamethyleneimide are soluble in hydrocarbon solvents; other of the of highly substituted lithium amide bases, such as lithium diisopropylamide are soluble in ether/hydrocarbon solvent mixtures containing less than two equivalents of the ether solvent per mole of the highly substituted lithium amide bases; however, more generally there should be at least two equivalents of the ethereal solvent per mole of highly substituted lithium base present in the ethereal/hydrocarbon solvent mixtures.

Other solvents which may be utilized include the highly substituted amine bases themselves, such as, e.g., hexamethyldisilazane, diisopropylamine and hexamethyleneimine, i.e., these bases may be used in excess as solvents in the preparation of their respective highly substituted lithium bases. This serves to raise the reaction temperature and thereby shorten the reaction time without requiring addition of a catalyst.

Reaction temperatures may be varied widely depending on the nature of the solvent system employed. For example, in tetrahydrofuran the reaction temperature may be varied from 0° C. up to the reflux temperature (66° C.), whereas, in an excess of hexamethyldisilazane the reaction temperature may be as high as 126° C.

The following examples further illustrate the invention. An argon atmosphere is utilized in all the examples.

EXAMPLE 1

Preparation of Lithium Hexamethyldisilazide (no solvent and no catalyst)

To an oven dried 250 ml, three-necked flask, equipped with a mechanical stirrer, a Claisen adapter fitted with a thermocouple, and cold finger condenser and an argon inlet was added 4.32 grams, (0.6225 moles) of lithium powder that contained 0.71% sodium and 87.7 grams (0.5434 moles) of hexamethyldisilazane (HMDS) (b.p. 127° C.). After heating the mixture to reflux (126° C.) for 3 hours, then cooling, and analysis, the solution was found to contain 21.8 wt % lithium hexamethyldisilazide (LHS). After heating the mixture to reflux for a further 2.5 hours and cooling to room temperature the mixture solidified. Tetrahydrofuran (148 grams) was then added, the mixture filtered, and the solids washed twice with an additional 20 ml of THF. The combined filtrates weighed 236.2 grams and contained 30.45 wt % LHS. This represented an 87% yield, after correction for the analytical samples removed during the reaction.

EXAMPLE 2

Preparation of Lithium Hexamethyldisilazide in THF (no catalyst)

To the equipment described above was added 10.66 grams (1.536 moles) of lithium powder, 116 grams of THF, and 51.5 grams of HMDS (0.319 moles). The reaction mixture was heated to reflux (72° C.). The extent of reaction was monitored by removing samples periodically and analyzing for LHS by active base titration. After 27 hours of reflux the mixture was allowed to cool to ambient temperature, filtered under argon, and the filter cake was washed twice with 30 ml of THF to yield 157 grams of solution. Analysis showed the solution to contain 26.95 wt % LHS. This represented an 87% yield, after correction for the analytical samples removed during the reaction.

EXAMPLE 3

Preparation of Lithium Hexamethyldisilazide in THF (using 0.095 mole % $FeCl_3$ as catalyst)

To a 2 liter, three-necked flask, equipped as described in Example 1, was added 33.82 grams (4.873 moles) of lithium powder and 758 grams of THF. The mixture was heated to 60° C. and a dropwise addition of 335 grams (2.074 moles) of HMDS begun. After 4.5% of the feed had been added a charge of 0.32 grams (0.0022 moles) of anhydrous ferric chloride was added to the reactor and the HMDS feed continued. The reaction temperature was kept between 57° and 61° C. thereafter. The overall feed time was 94 minutes. The mixture was stirred and heated for an additional 3 hours, cooled to room temperature, and filtered. The solids were washed twice with an additional 150 ml THF and the filtrates combined, to afford 1294 grams of solution, which contained 25.93 wt % LHS. The isolated yield of LHS was 97%.

EXAMPLE 4

Preparation of Lithium Hexamethyldisilazide in THF (using 1.18 mole % $TiCl_4$)

To the equipment described in Example 1 was added a mixture of 13.2 grams (1.90 moles) of 0.5 inch diameter lithium rod, cut in one centimeter long lengths and 122 grams of THF was added 49.1 grams (0.304 moles ) of HMDS and the mixture heated at 45° to 50° C. A charge of 0.682 grams (0.0036 moles) of $TiCl_4$ was added all at once to the reactor and the reaction temperature was maintained at 50° C. After 6.5 hours, an aliquot was withdrawn. Analysis indicated the yield of LHS was 75%. After a total of 12 hours heating at 50° C., the product solution was allowed to cool to ambient temperature, decanted away from the excess lithium metal, rinsed with 15 ml of THF to afford 164 grams of solution, which analyzed by titration as 25.41 wt. % LHS. This represented an 93% yield, after correction for the analytical samples removed during the reaction.

EXAMPLE 5

Preparation of Lithium Hexamethyleneimide in THF (no catalyst)

To a 500 ml three-necked flask, equipped as described in Example 1, was added a mixture of 7.27 grams (1.047 moles) of lithium powder and 200 ml of THF was added 61.7 grams (0.622 moles) of hexamethyleneimine and the reaction mixture heated to reflux. The extent of the reaction was monitored by removing samples periodically and analyzing for lithium amide by Watson-Eastham titration. After one hour of reflux the yield was 18%, and after 11.5 hours the yield was 97%. The reaction mixture was allowed to cool to ambient temperature, filtered, and the filter cake washed twice with 50 ml of tetrahydrofuran, to afford 242 grams of solution. This contained 19.9 wt % active lithium amide, as determined by Watson-Eastham titration, which represented an 84% yield.

What is claimed is:

1. A process for preparing high purity solutions of highly substituted lithium amide bases, comprising directly reacting lithium metal with highly substituted amine bases alone or in an ether solvent, a hydrocarbon solvent or in a mixed ether/hydrocarbon solvent mixture, at a temperature less than the melting point of lithium optionally in the presence of a catalyst selected from the group consisting of tin salts and transition metal salts of Groups 4B, 5B, 6B, 7B, and 8 of the Periodic Table to produce a solution of highly substituted lithium amide bases devoid of gaseous alkane by-products, reduced electron carrier residue, and solvent decomposition products.

2. The process of claim 1 wherein the highly substituted amine bases are selected from the group consisting of diisopropylamine, hexamethyleneimine, diisobutylamine, tert-butyl-methylamine, tert-butyl-trimethylsilylamine, cyclohexylisopropylamine, cyclohexylmethylamine, allyl-1-phenylethylamine, allyl-(R)-1-phenylethylamine, allyl-(S)-1-phenylethylamine, benzyl-1-phenylethylamine, benzyl-(R)-1-phenylethylamine, benzyl-(R)-1-phenylethylamine, bis-(1-phenylethyl)amine, (+)-bis-[(R)-1-phenylethyl]amine, (−)-bis-[(S)-1-phenylethyl]amine, 2,2,6,6-tetramethylpiperidine, pyrrolidine, piperidine and hexamethyldisilazane.

3. The process of claim 1 wherein the ether solvent is tetrahydrofuran.

4. The process of claim 1 wherein the mixed ether/hydrocarbon solvent is tetrahydrofuran/cyclohexane.

5. The process of claim 1 wherein the metal salt is selected from the group consisting of iron (III) chloride, iron (II) chloride, tin (II) chloride, tin (IV) chloride, titanium (IV) chloride and titanium (IV) isopropoxide.

6. High purity solutions of highly substituted lithium amide bases prepared by reacting lithium metal with a highly substituted amine base alone, in an ether solvent, a hydrocarbon solvent or in an ether/hydrocarbon solvent, at a temperature less than the melting point of the lithium metal, optionally in the presence of a catalyst selected from the group consisting of tin salts and transition metal salts of Groups 4B, 5B, 6B, 7B and 8 of the Periodic Table, wherein said solution is devoid of gaseous alkane by-products, reduced electron carrier residue, and solvent decomposition impurities.

7. The high purity solution of claim 6 in which the highly substituted lithium amide base is lithium hexamethyldisilazide and the ether solvent is tetrahydrofuran.

8. The high purity solution of claim 6 in which the highly substituted lithium amide base is lithium hexamethyldisilazide and the ether/hydrocarbon solvent is tetrahydrofuran/cyclohexane.

9. The high purity solution of claim 6 in which the highly substituted lithium amide base is lithium hexamethyleneimide and the ether solvent is tetrahydrofuran.

10. The high purity solution of claim 6 in which the highly substituted lithium amide base is lithium diisopropylamide and the ether/hydrocarbon solvent is tetrahydrofuran/cyclohexane.

11. The high purity solution of claim 6 in which the highly substituted lithium amide base is lithium hexamethyleneimide and the ether/hydrocarbon solvent is tetrahydrofuran/cyclohexane.

12. A high purity product solution of a highly substituted amide base in the same highly substituted base alone, in an ether solvent, in a hydrocarbon solvent or in an ether/hydrocarbon solvent mixture, optionally containing a catalytic amount of a salt selected from the group consisting of tin salts and transition metal salts of Groups 4B, 5B, 6B, 7B and 8 of the Periodic Table, which highly substituted amide base is selected from the group consisting of lithium diisopropylamide, lithium hexamethyleneimide, lithium diisobutylamide, lithium tert-butyl-methylamide, lithium tert-butyl-trimethylsilylamide, lithium cyclohexylisopropylamide, lithium cyclohexylmethylamide, lithium allyl-1-phenylethylamide, lithium allyl-(R)-1-phenylethylamide, lithium allyl-(S)-1-phenylethylamide, lithium benzyl-1-phenylethylamide, lithium benzyl-(R)-1-phenylethylamide, lithium benzyl-(R)-1-phenylethylamide, lithium bis-(1-phenylethyl) amide, lithium (+)-bis-[(R)-1-phenylethyl]amide, lithium (−)-bis-[(S)-1-phenylethyl]amide, lithium 2,2,6,6-tetramethylpeperidide, lithium pyrrolidide, lithium piperidide and lithium hexamethyldisilazide, wherein said solution is devoid of gaseous alkane by-products, reduced electron carrier residue, and solvent decomposition impurities.

13. A high purity product solution of a highly substituted amide base in the same highly substituted base alone, in an ether solvent, in a hydrocarbon solvent or in an ether/hydrocarbon solvent mixture, optionally containing a catalytic amount of a salt selected from the group consisting of tin salts and transition metal salts of Groups 4B, 5B, 6B, 7B and 8 of the Periodic Table, prepared at a temperature less than the melting point of lithium metal, which highly substituted amide base is selected from the group consisting of lithium diisopropylamide, lithium hexamethyleneimide, lithium diisobutylamide, lithium tert-butyl-methylamide, lithium tert-butyl-trimethylsilylamide, lithium cyclohexylisopropylamide, lithium cyclohexylmethylamide, lithium allyl-1-phenylethylamide, lithium allyl-(R)-1-phenylethylamide, lithium allyl-(S)-1-phenylethylamide, lithium benzyl-1-phenylethylamide, lithium benzyl-(R)-1-phenylethylamide, lithium benzyl-(R)-1-phenylethylamide, lithium bis-(1-phenylethyl) amide, lithium (+)-bis-[(R)-1-phenylethyl]amide, lithium (−)-bis-[(S)-1-phenylethyl]amide, lithium 2,2,6,6-tetramethylpeperidide, lithium pyrrolidide, lithium piperidide and lithium hexamethyldisilazide, wherein said solution is devoid of gaseous alkane by-products, reduced electron carrier residue, solvent decomposition impurities, and solvent decomposition impurities.

14. The composition of claim 12, wherein said ether solvent is selected from the group consisting of tetrahydrofuran, 2-methyltetrahydrofuran, diethyl ether, t-butylmethyl ether, dibutyl ether, diethoxymethane, 1,2-dimethoxyethane (glyme), diglyme, triglyme, and mixtures thereof.

15. The composition of claim 12, wherein said hydrocarbon solvent is selected from the group consisting of hexane, cyclohexane, toluene, ethylbenzene, and xylene and mixtures thereof.

* * * * *